US00RE36165E

United States Patent [19]

Behr

[11] E Patent Number: Re. 36,165

[45] Reissued Date of Patent: Mar. 30, 1999

[54] HEATING AND HUMIDIFYING RESPIRATORY MASK

[76] Inventor: R. Douglas Behr, 1509 Wood Pointe La., Apt. 1, Midland, Mich. 48642

[21] Appl. No.: 801,046

[22] Filed: Feb. 14, 1997

Related U.S. Patent Documents

Reissue of:

[64] Patent No.: 5,570,684
Issued: Nov. 5, 1996
Appl. No.: 581,040
Filed: Dec. 29, 1995

[51] Int. Cl.[6] ..... A62B 7/14

[52] U.S. Cl. ..... 128/204.17; 128/201.13; 128/205.25; 128/206.22

[58] Field of Search ..... 128/204.17, 201.13, 128/205.25, 205.27, 206.17, 206.24, 206.19, 206.22

[56] References Cited

U.S. PATENT DOCUMENTS

| | | | |
|---|---|---|---|
| 2,381,568 | 8/1945 | Booharin | 128/141 |
| 2,626,343 | 1/1953 | Fogel et al. | 219/46 |
| 2,741,246 | 4/1956 | Litchfield | 128/141 |
| 3,249,108 | 5/1966 | Terman | 128/146 |
| 3,326,214 | 6/1967 | McCoy | 128/212 |
| 3,333,585 | 8/1967 | Barghini et al. | 128/212 |
| 3,814,094 | 6/1974 | De Angelis et al. | 128/212 |
| 3,835,853 | 9/1974 | Turner | 128/212 |
| 4,136,691 | 1/1979 | Ebeling et al. | 128/201.13 |
| 4,150,671 | 4/1979 | Tiger | 128/212 |
| 4,196,728 | 4/1980 | Granite | 128/201.13 |
| 4,200,094 | 4/1980 | Gedeon et al. | 128/201.13 |
| 4,269,183 | 5/1981 | Hunt | 128/201.13 |
| 4,325,365 | 4/1982 | Barbuto | 128/201.13 |
| 4,458,679 | 7/1984 | Ward | 128/201.13 |
| 4,473,071 | 9/1984 | Hunt | 128/201.13 |
| 4,478,215 | 10/1984 | Hanlon | 128/201.13 |
| 4,601,287 | 7/1986 | Royce, Jr. | 128/204.17 |
| 4,620,537 | 11/1986 | Brown | 128/201.13 |
| 4,671,268 | 6/1987 | Hunt | 128/201.13 |
| 4,683,869 | 8/1987 | Wilcox | 126/204 |
| 4,793,343 | 12/1988 | Cummins, Jr. et al. | 128/204.17 |
| 4,829,997 | 5/1989 | Douwens et al. | 128/201.13 |
| 5,007,114 | 4/1991 | Numano | 2/206 |
| 5,010,594 | 4/1991 | Suzuki et al. | 2/206 |
| 5,086,766 | 2/1992 | Beacham | 128/203.27 |
| 5,433,192 | 7/1995 | Ebeling | 128/201.13 |
| 5,435,299 | 7/1995 | Langman | 128/201.13 |
| 5,595,173 | 1/1997 | Dodd, Jr. | 128/201.13 |

*Primary Examiner*—Aaron J. Lewis
*Assistant Examiner*—V. Srivastava
*Attorney, Agent, or Firm*—Christopher John Rudy

[57] ABSTRACT

A light-weight face mask can heat and humidify inhaled air with previously-exhaled air by passing the air through a highly-effective and highly-efficient heat exchanger disposed within the mask. The heat exchanger has a multitude of layers of metallic mesh through which the air passes generally linearly. The warm exhaled air heats the mesh which in turn heats the incoming air before it is inhaled. Moisture from the exhaled air condenses on the relatively-cool heat exchanger and humidifies the incoming air. Inhaled air enters the mask generally upwardly, and exhaled air exits it generally downwardly.

24 Claims, 1 Drawing Sheet

HEATING AND HUMIDIFYING RESPIRATORY MASK

Matter enclosed in heavy brackets [ ] appears in the original patent but forms no part of this reissue specification; matter printed in italics indicates the additions made by reissue.

*CROSS-REFERENCE*

*This is a reissue of Pat. No. 5,570,684 (Nov. 5, 1996) which issued from Ser. No. 08/581,040 which was filed on Dec. 29, 1995.*

BACKGROUND OF THE INVENTION

*I. Field of the Invention*

*The present invention concerns a respiratory mask. The mask is useful in cold weather for heating and humidifying inhaled air with exhaled air through a heat exchanger.*

*II. Description of Known Art*

The detrimental effects of breathing cold air, particularly for people with medical problems such as cardiac conditions, angina, and asthma, and the benefits of heating inhaled air have been recognized for many decades and are described in various publications including U.S. Pat. Nos. 3,835,853; 4,325,365; 4,601,287; 4,793,343; and 4,829,997. Inhaled air has been heated with electrical elements as taught in U.S. Pat. Nos. 2,626,343; 3,249,108; 4,601,287; 4,620,537; and 4,793,343, and with heated water as taught in U.S. Pat. No. 5,086,766. Inhaled air has been heated also by devices that obtain heat from portions of the human body rather than external power sources as described [is] *in* U.S. Pat. Nos. 4,269,183, 4,473,071, 4,671,268, and 4,683,869. The advantage of heating the inhaled air with humid exhaled air has been recognized for many decades. U.S. Pat. Nos. 3,326,214, 3,333,585, 3,814,094, and 4,136,691, *and* 4,478,215 teach heating and humidifying inhaled air through exhaled air by passing the air through an exchanger fabricated from either foil, a nonwoven resilient porous fibrous organic polymeric material, a foraminous [heat conductive] *heat-conductive* material, or a continuous strip of wire netting wound helically. In addition, U.S. Pat. Nos. 4,150,671, 4,196,728, 4,200,094, 4,325,365, and 4,458,679 teach heating inhaled air with [one of] the following: a conduit having heat-exchanging fins; a flexible curved horn of expanding cross section, having a flared internal chamber containing metal mesh; a spool-like member having a series of transverse notches which leave integral fins; an elongated curved housing in which is disposed a plurality of pairs of spaced-apart vanes; or a counter-current medium such as a metal sponge. U.S. Pat. No. 3,835,853 teaches an improved device for heating inhaled air with exhaled airs which avoids ice formation at very low temperatures by bypassing a portion of the inhaled air with an automatic valve. Some of these patents, e.g., U.S. Pat. No. 4,478,215, teach that the inhaled air is humidified as well as heated by the exhaled air.

None of the disclosed devices for heating air for breathing is in widespread use. Generally, the effective devices are heavy and bulky. In addition, many are relatively costly to produce.

*Furthermore, these additional U.S. patents are cited:*

*U.S. Pat. No. 2,381,568—Gas Mask.*

*U.S. Pat. No. 2,741,246—Gas Masks.*

*U.S. Pat. No. 5,007,114—Humidity-retaining Mask.*

*U.S. Pat. No. 5,010,594—Dampening Mask for Use in Aircraft.*

*U.S. Pat. No. 5,433,192—Breathing Mask having a Cellulose Heat and Moisture Exchanger Formed Therein.*

*U.S. Pat. No. 5,595,173—Rehumidification Filter for Ventilation Mask.*

*U.S. Pat. No. 5,435,299—Respiratory Mask.*

*DESIDERATA*

Widespread use of a device for warming air that is breathed in requires that the device be relatively small, light weight, and inexpensive. These characteristics demand that the heat exchanger be simple, and yet highly efficient and highly effective.

SOME OBJECTS AND AN INTRODUCTORY SUMMARY OF THE INVENTION

The first objective of this invention is to provide a face mask having a highly effective heat exchanger for heating and humidifying inhaled air with exhaled air.

The second objective of this invention is to provide a heat exchanger that is highly efficient in order to minimize weight, bulk, and cost so that the mask is suitable for widespread use in many activities such as shoveling snow, snow skiing, and jogging.

The third objective of this invention is to provide a device that offers negligible resistance to air flow.

The fourth objective of this invention is to have a relatively low air volume and low retention of carbon dioxide.

The fifth objective of the invention is to provide simple means, having no external power source, for reducing the tendency of the heat exchanger to freeze in cold weather, especially when snow is falling or blowing.

The sixth objective of the invention is to provide a device that can easily and quickly be removed and safely washed or sterilized, even in a dish washer.

*As may pertain to certain embodiments of this invention, the following is noted:*

The first objective was achieved, in part, by constructing a heat exchanger from about 15 layers or more of metallic mesh, having high surface area, high thermal conductivity within the layer, and low thermal conductivity layer to layer. This configuration allows a temperature differential to develop in the direction of air flow. The first two objectives are attained in part by fabricating the shell of the mask from a material having low thermal conductivity and by providing a small air space between the mask and face, except at the edges of the mask. The edges of the mask contact the face, providing a seal that inhibits flow of air at the edges. The second, third, and fourth objectives are attained in part by having the heat exchanger consist of no more than about 50 layers of metallic mesh having a cross-sectional area of no more than about 24 square centimeters, and the thickness of the multitude of layers no more than about 2.5 centimeters when compressed. The larger the area of the heat exchanger exposed to the cold environment becomes: the greater is the cooling of the heat exchanger by means of conduction and radiation. Therefore, limiting the cross-sectional area of the outer layer to about 24 square centimeters contributes, in part, to the fifth objective. The fifth objective is attained, in part, by having the opening of the mask face generally downward so that inhaled air enters the mask in a generally upward direction, and, in part, by locating at least a portion of the outermost layers of mesh in the heat exchanger several centimeters above the lower extremity of the opening in the mask. The sixth objective is attained by the simplicity of both the face mask and the heat exchanger disposed in the mask, and by holding the mask in place with a strap assembly that can be placed easily and quickly around a person's head.

BRIEF DESCRIPTION OF THE DRAWINGS

The detail of this invention and its operation together with additional objectives can best be understood by the following description *taken* in connection with the drawings, in which.

Figure 1:
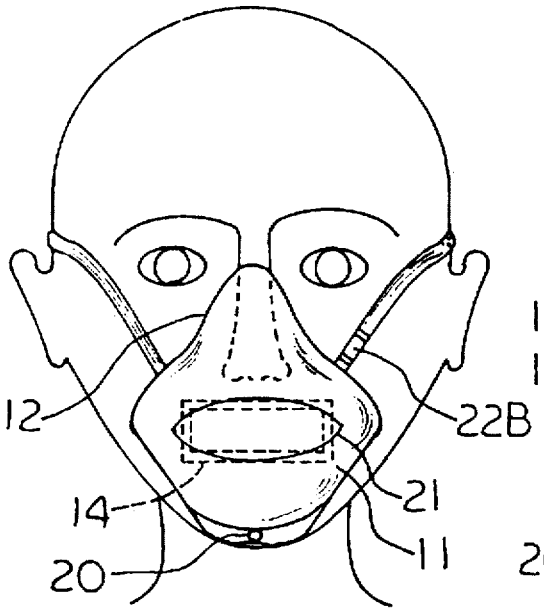
FIG. 1 is a front elevational view of a preferred embodiment of the mask worn by a person.
Figure 2:
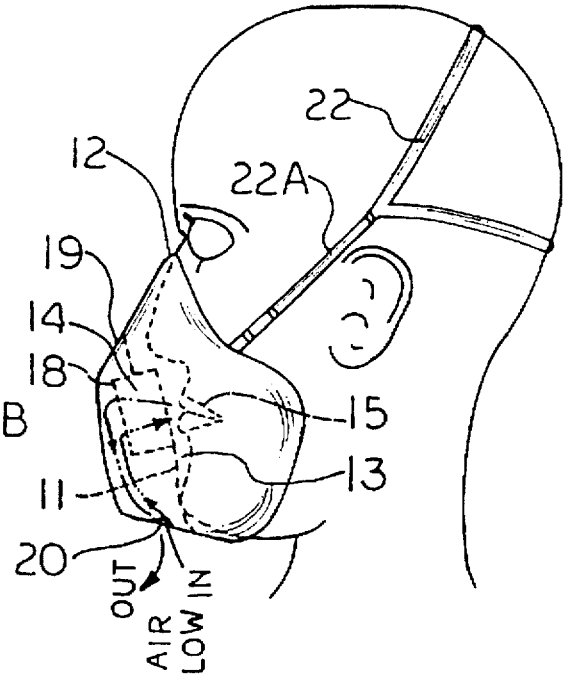
FIG. 2 is a side elevational view of the mask of FIG. 1.
Figure 3:
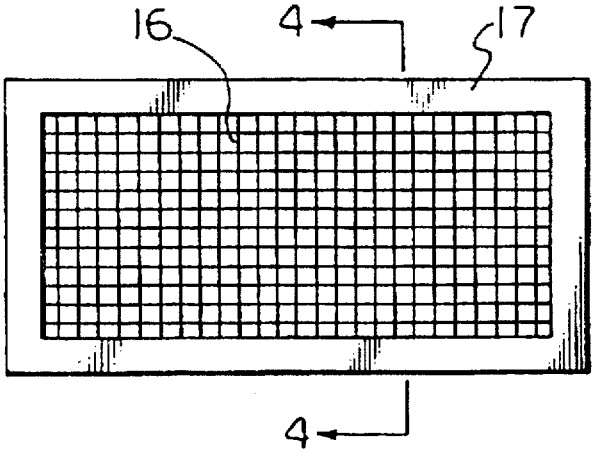
FIG. 3 is an enlarged view of a heat exchanger for the mask of FIG. 1.
Figure 4:
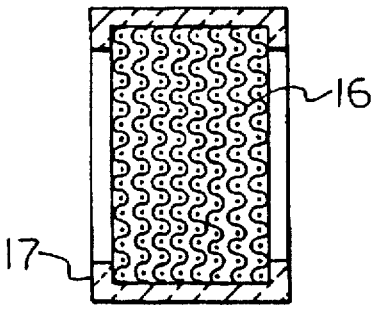
FIG. 4 is a cross-sectional view of the heat exchanger taken along line 4—4 of FIG. 3.

DESCRIPTION OF THE PREFERRED EMBODIMENT AND ADDITIONALLY ILLUSTRATIVE DETAIL OF THE INVENTION

With continuing reference to the drawings wherein numbers indicate components, reference number 11 indicates an inner shell of the mask, which has low thermal conductivity and which covers the lower portion of the face. The inner shell fits tightly to the face around the entire peripheral edge 12 to *form a seal and* prevent air flow *therethrough*. The remainder of the inner shell is spaced apart from the face, providing a dead air space 13, said air space providing thermal insulation. The air space is small in order to reduce the amount of entrapped carbon dioxide. A highly-effective heat exchanger 14 is centrally located approximately in front of the mouth 15 of the wearer. Said heat exchanger comprises a multitude of layers of metallic mesh 16, each layer having a large surface area, high thermal conductivity within the layer, and low thermal conductivity to adjacent layers. The collection of layers of metallic mesh are held together as a bundle along at least one edge by means such as a formed plastic frame 17. Said bundle of metallic mesh fits snugly in a pocket 18 that is an integral part of the inner shell. Because of the snug fit of the heat exchanger in the pocket and the tight fit of the periphery of the inner shell on the face of the person wearing the mask, essentially all inhaled and exhaled air flows generally linearly through the multitude of layers of metallic mesh in the heat exchanger. Outer shell 19 is generally spaced apart from the inner shell and from the outer extremity of the heat exchanger. The sides and top of the outer shell 19 join the inner shell above and on each side of the heat exchanger. The inner and outer shells are spaced apart along the bottom of the mask, providing an opening 20. Exhaled air is deflected downward by the outer shell and exits generally downward from said opening, thereby reducing fogging of glasses or goggles by exhaled air. Inhaled air enters generally upward through said opening, thereby reducing the tendency for snow that is falling or blowing from entering said opening and thereby reducing clogging and freezing of the heat exchanger. The heat exchanger is located well above the lower edge of the opening, thereby additionally reducing loss of heat via radiation and reducing the tendency for snow to enter the heat exchanger and freeze *it*. One should realize that the latter two design features are relatively simple and much more practical than heating the heat exchanger with an external power source such as batteries or heated water. The mask can be produced in any color including skin tones. Facial expressions such as *with feature* 21 can be printed, drawn, or painted on the front of the mask. The mask is held in place by the strap assembly 22. It can have an elastic portion 22A [or] *and/or* an adjustable interlocking portion 22B to facilitate adjustment and removal of the mask.

Experiments were conducted to determine the effectiveness of the invention in heating inhaled air. A commercial respirator was modified for the experiments. Tape was placed over two input ports, and the centrally-located output port was enlarged to a diameter of about 4.5 centimeters. A rectangular pocket for a heat exchanger was fabricated *to be* about 4.5 centimeters high and about 5.7 centimeters long, and *it* placed within the mask in front of the round opening. The space around the pocket was partially filled with a silicone caulk to hold the pocket in place and leave a relatively small gap between the caulk and the face. Thirty layers of metallic mesh, about 4.5 by 5.7 centimeters, were placed in the heat-exchanger pocket. The mesh was comprised of aluminum wires about 0.025 centimeters in diameter, spaced about 0.16 centimeters apart center to center in one direction and spaced apart about 0.14 centimeters in the perpendicular direction. Temperature of the air was measured inside the mask immediately adjacent to the inner layer of mesh while breathing through the mask. Temperature measurements were made with a Digitherm electronic indoor/outdoor thermometer. The remote sensor that was placed inside the mask was about 0.6 centimeters [thick] *high* and about 1.6 centimeters in diameter. With an outdoor temperature of 33.4 degrees F., and a body temperature of 97.5 degrees F., the air temperature in the mask stabilized at 87.8 degrees F., after 2 minutes. Assuming that the measured temperature, M, is the average of the temperature of the air entering the mask from the heat exchanger, H, and *of* the temperature of the air breathed out of the mouth, B, then M=(B+H)/2, and H=2M−B. In this case, H=2(87.8) −97.5=78.1 degrees F. In this example, the mask heated the outside air 44.7 degrees F. The most that the mask could heat the air is 97.5−33.4=64.1 degrees F. The percent effectiveness is 100% times the ratio of the measured increase in temperature to the difference between body and outdoor temperatures. In this example, the percent effectiveness is 100%(44.7 *degrees F.*/64.1 *decrees F.*)=70%. This data and similar data are tabulated below. All temperatures are given in degrees Fahrenheit, i.e., F.

| | | | | | |
|---|---|---|---|---|---|
| Number of layers of mesh | 30 | 8 | 16 | 20 | 30 |
| Outside temperature | 33.4 | 36.1 | 36.1 | 36.1 | 36.1 |
| Measured temperature | 87.8 | 82.7 | 83.3 | 86.3 | 88.3 |
| Calculated input air temperature | 78.1 | 67.9 | 69.1 | 74.7 | 79.1 |
| Increase in temperature | 44.7 | 31.8 | 33.0 | 38.6 | 43.0 |
| Percent effectiveness | 70 | 52 | 54 | 63 | 70 |

| | Type of mesh | | | | |
|---|---|---|---|---|---|
| | "standard" | | "fine" | | none |
| Number of layers of mesh | 16 | 32 | 16 | 32 | 0 |
| Outside temperature | 17.7 | 17.9 | 18.3 | 18.5 | 18.7 |
| Measured temperature | 80.7 | 84.9 | 84.7 | 89.4 | 72.0 |
| Calculated input air temperature | 63.9 | 72.3 | 71.9 | 81.3 | 46.5 |
| Increase in temperature | 46.2 | 54.4 | 53.6 | 62.8 | 27.2 |
| Percent effectiveness | 57 | 68 | 68 | 79 | 35 |

One can see from this data that the mask heats the inhaled air to some extent even with no metallic mesh in the heat-exchanger pocket, and that the amount of heating increased with increasing number of layers to nearly 80 percent effectiveness. One can also see that the "fine" mesh was more effective than the "standard" mesh for a selected number of layers. On the other hand, the "fine" mesh had about 4 times the number of wires in a selected area, and therefore, each layer of "fine" mesh was 4 times as heavy as the "standard" mesh. One can also see that 32 layers of "standard" mesh was as effective in heating air as 16 layers of the "fine" mesh, even though 32 layers of "standard" mesh weighed half as much as 16 layers of "fine" mesh. Even with thirty-six layers of standard mesh in the heat exchanger, no resistance to breathing was evident. The pressure differential between the inside of the mask was measured while a person was breathing through it. The pressure differential was less than about 0.02 inches of water column during normal breathing and less than about 0.1 inches of water when breathing was as fast as possible.

The invention accordingly *or by incorporation of features from originally filed claims* includes the following embodiments:

A light-weight respiratory face mask for warming and humidifying inhaled air efficiently with negligible pressure differential, which includes the following: an inner flexible shell covering the face from the nose to the chin, the inner shell generally spaced apart from the face, which provides an insulating air space between the face and the mask, with peripheral edges of the inner shell contacting the face to form an air seal; a heat exchanger disposed in a pocket in the inner shell located opposite the mouth, and in open communication with the mouth, with the heat exchanger consisting of about 15 to 50 layers of metallic mesh, each of the layers having a high surface area and having high thermal conductivity within the layer and low thermal conductivity to adjacent layers; an outer shell opposite the mouth, the outer shell joining the inner shell above and on either side of the heat exchanger, and the outer shell spaced apart from the heat exchanger and the inner shell; an opening between the inner shell and the outer shell below the heat exchanger to allow entry of inhaled air generally upward and discharge of exhaled air generally downward such that exhaled air heats the heat exchanger which in turn heats the inhaled air. In addition, the mask can include the following features: its outer shell can be such as to protrude less than about 3 centimeters beyond the wearer's nose; the surface area of metal in the heat exchanger can be substantially less than about two thousand square centimeters (about three hundred square inches); each layer of the heat exchanger can have an area of 6 to 24 square centimeters; the thickness of the multitude of metallic layers can be less than 2.5 centimeters when pressed together; the layers of mesh can be aluminum or brass; the layers of mesh can be aluminum screening that consists of aluminum wires about 0.025 centimeters in diameter, spaced about 0.141 centimeters center to center in one direction and spaced about 0.159 centimeters apart in the perpendicular direction; at least a portion of [of] the outer layer of mesh in the heat exchanger can be at least two centimeters above the lower edge of the opening in the mask; adjacent layers of metallic mesh can be connected along at least one edge; the heat exchanger can be centrally located, and the width of the heat exchanger can exceed the height; a flexible cavity can be provided within the mask for easily and quickly inserting and removing a heat exchanger pack consisting of layers of metallic mesh; it can have the color of one of the many flesh tones; it can have facial expressions drawn, painted, or printed on the frontal surface; it can have attached to each edge a strap assembly which passes around the wearer's head, thereby holding the mask in place, and the strap assembly can be attached with at least one adjustable interlocking component, and it can have at least a portion of the strap assembly elastic.

As can be appreciated from the foregoing and the drawings, the layers of metallic mesh can be provided in a sheetlike arrangement, one layer upon another. They can be such that air can flow back and forth across the layered arrangement in a direction from outside layer to inside layer and from inside layer to outside layer in a direction substantially perpendicular to the layers in the mask during breathing by the mask wearer.

And accordingly, this invention can relate to a light-weight face mask for heating and humidifying inhaled air with previously-exhaled air by passing the air through a highly-effective, highly-efficient heat exchanger disposed within the mask, with the heat exchanger consisting of a multitude of layers of metallic mesh through which the air passes generally linearly. The warm exhaled air heats the mesh which in turn heats the incoming air before it is inhaled. Moisture from the exhaled air condenses on the relatively cool heat exchanger and humidifies the incoming air. Inhaled air enters the mask generally upwardly, and exhaled air exits it generally downwardly.

It will be understood that certain features and subcombinations have utility and may be used without reference to other features and subcombinations. This is contemplated and within the scope of my claims. It is further [obvious] *plain* that various changes may be made in details within the scope of my claims without departing from the spirit of my invention. It is to be understood, therefore, that my invention is not to be limited to the specific details shown and described.

*Accordingly, a mask of the invention can include a multi-layered metallic mesh heat exchanger enclosed inside the mask and has an opening below the heat exchanger in the outer shell for inhalation and exhalation. Along these lines, the invention can include a respiratory face mask which can be worn by a person, i.e., a wearer, who has a head, including a face, which mask includes an inner shell, with an edge thereof able to be placed in contact with the wearer's face to form an air seal when the mask is worn; a heat exchanger disposed in the mask, including a multitude of layers of metallic mesh, the layers being provided in a sheetlike arrangement, one layer upon another, and being such that air can flow back and forth across the layered arrangement in a direction from outside layer to inside layer and from inside layer to outside layer in a direction substantially perpendicular to the layers in the mask during breathing by the wearer; an outer shell, generally spaced apart from the inner shell and the heat exchanger, which can deflect exhaled air downwardly through an opening when the mask is worn and the wearer's head is in an upright position; the opening being below the heat exchanger to allow entry of air inhaled by the wearer of the mask when the mask is worn and the wearer's head is in an upright position upwardly, and discharge of air exhaled by the wearer of the mask when the mask is worn and the wearer's head is in an upright position downwardly—such that exhaled air can heat the heat exchanger, which in turn can heat the inhaled air—with the outer shell, the opening and the heat exchanger being located on the mask so as to be able to reduce a tendency of the heat exchanger to otherwise freeze in cold weather when the mask is worn when snow is falling or blowing, wherein the mask is useful for warming and humidifying inhaled air efficiently.*

Having described my invention, what I claim is:

1. A light-weight respiratory face mask for warming and humidifying inhaled air of a person who can wear the mask, i.e., a wearer, and who has a head, and a face, nose, chin and mouth, efficiently with negligible pressure differential, which comprises:

(a) an inner flexible shell capable of covering the wearer's face from the nose to the chin, said shell capable of being spaced apart from the wearer's face, and capable of providing an insulating air space between the wearer's face and the mask when the mask is worn, with peripheral edges of the inner shell able to be placed in contact with the wearer's face to form an air seal when the mask is worn;

(b) a heat exchanger disposed in a pocket in the inner shell located opposite a position which can define the wearer's mouth, and to be in open communication with the wearer's mouth, with the heat exchanger consisting of about 15 to about 50 layers of metallic mesh, and with each of the layers of the metallic mesh having a surface area and a thermal conductivity within each layer of the metallic mesh appropriate to the metallic mesh employed and low thermal conductivity to adjacent layer(s) of the metallic mesh, the layers being provided in a sheetlike arrangement, one layer upon another, and being such that air can flow back and forth across the layered arrangement in a direction from outside layer to inside layer and from inside layer to outside layer in a direction substantially perpendicular to the layers in the mask during breathing by the wearer;

(c) an outer shell in a position opposite the wearer's mouth when the mask is worn, with the outer shell having edges and joining the inner shell above and on either side of the heat exchanger, and the outer shell spaced apart from the heat exchanger and the inner shell;

(d) an opening between the inner shell and the outer shell below the heat exchanger to allow entry of air inhaled by the wearer of the mask when the mask is worn and the wearer's head is in an upright position upwardly, and discharge of air exhaled by the wearer of the mask when the mask is worn and the wearer's head is in an upright position downwardly, such that exhaled air can heat the heat exchanger, which in turn can heat the inhaled air, with the outer shell, the opening and the heat exchanger being located on the mask so as to be able to reduce a tendency of the heat exchanger to otherwise freeze in cold weather when the mask is worn when snow is falling or blowing.

2. The mask of claim 1, wherein the outer shell protrudes less than about 3 centimeters beyond the wearer's nose.

3. The mask of claim 1, wherein the total surface area of all of the layers of metallic mesh in the heat exchanger is substantially less than about two thousand square centimeters.

4. The mask of claim 1, wherein each layer of the metallic mesh of the heat exchanger has a cross-sectional area of 6 to 24 square centimeters.

5. The mask of claim 4, wherein the thickness of the metallic layers is less than 2.5 centimeters when pressed together.

6. The mask of claim 1, wherein the layers of the metallic mesh are of aluminum or brass.

7. The mask of claim 6, wherein each of the layers of the metallic mesh is of aluminum screening which consists of aluminum wires about 0.025 centimeters in diameter, spaced about 0.14 centimeters apart center to center in one direction and spaced about 0.16 centimeters apart center to center in a direction perpendicular thereto.

8. The mask of claim 1, wherein at least a portion of [of] the outer layer of metallic mesh in the heat exchanger is at least two centimeters above the lower edge of the opening in the mask.

9. The mask of claim 1, wherein adjacent layers of metallic mesh are connected along at least one edge.

10. The mask of claim 4, wherein the heat exchanger is centrally located, and the heat exchanger had a width and a height, and the width of the heat exchanger exceeds the height of the heat exchanger.

11. The mask of claim 10, wherein a flexible cavity is provided within the mask for easily and quickly inserting and removing a heat exchanger pack consisting of layers of metallic mesh.

12. The mask of claim 1, having a color of a flesh tone.

13. The mask of claim 1, having facial expressions drawn, painted, or printed thereon.

14. The mask of claim 1, having attached to edges thereof a strap assembly which can pass around the wearer's head so as to hold the mask in place.

15. The mask of claim 14, wherein the strap assembly is attached with at least one adjustable interlocking component.

16. The mask of claim 14, wherein at least a portion of the strap assembly is elastic.

17. A respiratory face mask capable of being worn by a person, i.e., a wearer, who has a head, and a face, nose, chin and mouth, which mask comprises the following:

an inner flexible shell capable of covering the wearer's face from the nose to the chin, said shell capable of being spaced apart from the wearer's face, and capable of providing an insulating air space between the wearer's face and the mask when the mask is worn, with peripheral edges of the inner shell able to be placed in contact with the wearer's face to form an air seal when the mask is worn;

a heat exchanger disposed in a pocket in the inner shell located opposite a position which can define the wearer's mouth, and to be in open communication with the wearer's mouth, with the heat exchanger including a multitude of layers of metallic mesh, the layers being provided in a sheetlike arrangement, one layer upon another, and being such that air can flow back and forth across the layered arrangement in a direction from outside layer to inside layer and from inside layer to outside layer in a direction substantially perpendicular to the layers in the mask during breathing by the wearer;

an outer shell having edges and joining the inner shell above and on either side of the heat exchanger, with the outer shell being spaced apart from the heat exchanger and the inner shell;

an opening between the [the] inner shell and the outer shell below the heat exchanger to allow entry of air inhaled by the wearer of the mask when the mask is worn and the wearer's head is in an upright position upwardly, and discharge of air exhaled by the wearer of the mask when the mask is worn and the wearer's head is in an upright position downwardly—such that exhaled air can heat the heat exchanger, which in turn can heat the inhaled air—with the outer shell, the opening and the heat exchanger being located on the mask so as to be able to reduce a tendency of the heat exchanger to otherwise freeze in cold weather when the mask is worn when snow is falling or blowing, wherein the mask is light-weight and useful for warming and humidifying inhaled air efficiently with negligible pressure differential for the wearer.

18. The mask of claim 17, wherein the multitude of layers of the metallic mesh in the heat exchanger is from about 8 to about 50 layers of metallic mesh, and the heat exchanger includes an outer layer with a cross-sectional area to the outer layer of the heat exchanger of no more than 24 square centimeters.

19. The mask of claim 18, wherein the mask has an effectiveness of warming outside air of at least 57 percent when the outside air temperature is 17.7 degrees Fahrenheit.

20. The mask of claim 19, wherein the effectiveness of warming the outside air is at least 70 percent when the outside air temperature is 33.4 degrees Fahrenheit.

*21. In a respiratory face mask including a facepiece and a metallic heat exchanger, said mask useful for warming and humidifying cold outside air wherein inhaled air comes directly into the mask from the outside air through the heat exchanger, and exhaled air goes from inside the mask through the heat exchanger directly to the outside air, the improvement which comprises an outer shell attached to the facepiece in a front part of the mask with the heat exchanger being a multi-layered metallic mesh heat exchanger enclosed inside the mask behind the outer shell, with an opening to the outside air provided below the multi-layered metallic mesh heat exchanger in the outer shell of the mask for inhalation and exhalation therethrough, wherein the opening and the multi-layered metallic mesh heat exchanger are located on the mask so as to be able to reduce a tendency of the heat exchanger to otherwise freeze in cold weather when the mask is worn when snow is falling or blowing.*

*22. A respiratory face mask which can be worn by a person, i.e., a wearer, who has a head, including a face, which mask comprises the following:*

*an inner shell, with an edge thereof able to be placed in contact with the wearer's face to form an air seal when the mask is worn;*

*a heat exchanger disposed in the mask, including a multitude of layers of metallic mesh, the layers being provided in a sheetlike arrangement, one layer upon another, and being such that air can flow back and forth across the layered arrangement in a direction from outside layer to inside layer and from inside layer to outside layer in a direction substantially perpendicular to the layers in the mask, and substantially perpendicular to the face of the wearer, during breathing by the wearer;*

*an outer shell, generally spaced apart from the inner shell and the heat exchanger, which can deflect exhaled air downwardly to outside air through an opening when the mask is worn and the wearer's head is in an upright position;*

*the opening being below the heat exchanger to allow entry of air inhaled by the wearer of the mask when the mask is worn and the wearer's head is in an upright position upwardly, and discharge of air exhaled by the wearer of the mask when the mask is worn and the wearer's head is in an upright position downwardly—such that exhaled air can heat the heat exchanger, which in turn can heat the inhaled air—with the outer shell, the opening and the heat exchanger being located on the mask so as to be able to reduce a tendency of the heat exchanger to otherwise freeze in cold weather when the mask is worn when snow is falling or blowing,*

*wherein the mask is useful for warming and humidifying inhaled air efficiently,*

*and wherein the inhaled air comes directly into the mask from the outside air through the heat exchanger, and the exhaled air goes from inside the mask through the heat exchanger directly to the outside air.*

*23. The mask of claim 22, wherein the multitude of layers of the metallic mesh in the heat exchanger are from about 8 to about 50 layers of metallic mesh.*

*24. The mask of claim 23, wherein the multitude of layers of the metallic mesh is of aluminum or brass.*

* * * * *